US012796907B2

(12) United States Patent
Sinha et al.

(10) Patent No.: US 12,796,907 B2
(45) Date of Patent: Nov. 17, 2026

(54) MONITORING OPHTHALMIC CONDITIONS USING A HEADSET

(71) Applicant: Verily Life Sciences LLC, Dallas, TX (US)

(72) Inventors: Supriyo Sinha, Menlo Park, CA (US); Prachi Shah, Santa Clara, CA (US); Kirk Gossage, Pacifica, CA (US); Alexandre Tumlinson, San Leandro, CA (US); Dimitri Azar, Chicago, IL (US)

(73) Assignee: Verily Health Inc., Dallas, TX (US)

(*) Notice: Subject to any disclaimer, the term of this patent is extended or adjusted under 35 U.S.C. 154(b) by 359 days.

(21) Appl. No.: 18/514,590

(22) Filed: Nov. 20, 2023

(65) Prior Publication Data

US 2025/0160637 A1 May 22, 2025

(51) Int. Cl.
*A61B 5/11* (2006.01)
*A61B 3/00* (2006.01)
(Continued)

(52) U.S. Cl.
CPC ................ *A61B 3/005* (2013.01); *A61B 3/14* (2013.01); *A61B 5/1103* (2013.01); *A61B 5/746* (2013.01)

(58) Field of Classification Search
CPC ......... A61B 3/14; A61B 3/152; A61B 3/0008; A61B 3/0091; A61B 3/102; A61B 3/13;
(Continued)

(56) References Cited

U.S. PATENT DOCUMENTS 11,294,459 B1 * 4/2022 Richman .............. G06V 40/197
11,360,313 B1 6/2022 Fernandez
(Continued)

FOREIGN PATENT DOCUMENTS

CN 109276420 A 1/2019
KR 101966164 B1 7/2018

OTHER PUBLICATIONS

"Through A New Lens: The Promise Of Virtual Reality For Enhancing Vision Therapy;" Forbes.com; https://www.forbes.com/sites/williamhaseltine/2023/09/17 /through-a-new-lens-the-promise-of-virtual-reality-for-enhancing-vision-therapy/?sh=214cdc4 . . . ; Sep. 17, 2023; 8 pages.

*Primary Examiner* — Brandi N Thomas
(74) *Attorney, Agent, or Firm* — Christensen O'Connor Johnson Kindness PLLC

(57) ABSTRACT

Disclosed is a system for monitoring ophthalmic conditions. The system includes a headset configured to be worn by a user and a device. The headset includes a display and an ophthalmic testing unit comprising one or more sensors to obtain sensor information indicating a physiological measurement of an eye of the user. The device includes a processor to execute instructions stored in a memory to: receive surgical information, from a data structure, corresponding to a first time in which a physiological measurement of the eye is obtained; receive sensor information, from the headset, corresponding to a second time in which a physiological measurement is obtained; and generate an ophthalmic score based on a comparison between the surgical information and the sensor information. Other aspects are also described and claimed.

22 Claims, 13 Drawing Sheets

(51) Int. Cl.
*A61B 3/14* (2006.01)
*A61B 5/00* (2006.01)

(58) Field of Classification Search
CPC . A61B 3/0083; A61B 2090/3735; A61B 3/18; A61B 5/0013; A61B 5/6803; A61B 5/0066; G06V 40/19; G06V 40/18; A61F 2/1662; A61F 9/00736; G02B 21/0012; G02B 21/084; G02B 27/0075
See application file for complete search history.

(56) References Cited

U.S. PATENT DOCUMENTS

| | | | | |
|---|---|---|---|---|
| 2006/0287906 | A1* | 12/2006 | McGillin | G06Q 10/06311 705/7.14 |
| 2017/0007450 | A1 | 1/2017 | Samec et al. | |
| 2018/0246568 | A1* | 8/2018 | Holz | G06V 40/20 |
| 2019/0159956 | A1 | 5/2019 | Koziak | |
| 2019/0366030 | A1 | 12/2019 | Giap et al. | |
| 2019/0374100 | A1 | 12/2019 | Okazaki et al. | |
| 2020/0138669 | A1 | 5/2020 | Berdahl et al. | |
| 2020/0359886 | A1 | 11/2020 | Azar et al. | |
| 2023/0146429 | A1* | 5/2023 | Pisheh | A61B 3/1216 351/206 |

* cited by examiner

MONITORING OPHTHALMIC CONDITIONS USING A HEADSET

TECHNICAL FIELD

This disclosure relates generally to monitoring ophthalmic conditions and, more specifically, to monitoring ophthalmic conditions using a headset. Other aspects are also described.

BACKGROUND

Different surgical procedures exist today for ophthalmic conditions. For example, photorefractive keratectomy (PRK), laser epithelial keratomileusis (LASEK), refractive lens exchange, corneal transplants, glaucoma surgery, retinal detachment surgeries, and vitrectomy are examples of ophthalmic surgeries that may be performed using various techniques. However, these surgeries may come with post-surgical symptoms and/or complications that should be monitored. For example, some post-surgical symptoms and/or complications may include blurriness of vision, dry eyes, inflammation of the eye, red-blood shot eyes, damage to blood vessels, drooping eyelids, dislocation of artificial lenses, and warping or distortion of the visual field.

The information included in this Background section of the specification, including any references cited herein and any description or discussion thereof, is included for technical reference purposes and is not to be regarded as subject matter by which the scope of the disclosure is to be bound.

SUMMARY

Implementations of this disclosure include utilizing a portable headset and a companion device to monitor eyes of a patient, and to evaluate recovery of the patient, for an ophthalmic condition. For example, the recovery could be from PRK, LASEK, refractive lens exchange, corneal transplants, glaucoma, retinal detachment, or vitrectomy. In some implementations, the system may include a headset configured to be worn by a user (e.g., the patient) and a device in communication with the headset. The headset may include a display, such as a virtual reality (VR), augmented reality (AR), or mixed reality (MR) display. The headset may also include an ophthalmic testing unit comprising one or more sensors (e.g., pupil detectors and/or retinal detectors). The sensors may be used to obtain sensor information indicating a physiological measurement of an eye of the user. For example, the physiological measurement could comprise a measure of visual acuity, drooping eye lids, blink pattern, blood vessels, inflammatory cells, intraocular pressure (IOP), muscle movement, corneal curvature, or pupil response. The device may include a processor configured to execute instructions stored in a memory to perform various steps, including receiving surgical information and sensor information. For example, the device can receive the surgical information from a data structure. The surgical information may correspond to a first time in which a physiological measurement of the eye is obtained. For example, the surgical information may correspond to a condition of the eye in connection with PRK, LASEK, refractive lens exchange, corneal transplants, glaucoma, retinal detachment, or vitrectomy. The device can also receive the sensor information from the headset. The sensor information may correspond to a second time in which a physiological measurement is obtained via the headset. The device can then generate an ophthalmic score based on a comparison between the surgical information and the sensor information. Other aspects are also described and claimed.

The above summary does not include an exhaustive list of all aspects of the present disclosure. It is contemplated that the disclosure includes all systems and methods that can be practiced from all suitable combinations of the various aspects summarized above, as well as those disclosed in the Detailed Description below and particularly pointed out in the Claims section. Such combinations may have particular advantages not specifically recited in the above summary.

BRIEF DESCRIPTION OF THE DRAWINGS

Several aspects of the disclosure here are illustrated by way of example and not by way of limitation in the figures of the accompanying drawings in which like references indicate similar elements. It should be noted that references to "an" or "one" aspect in this disclosure are not necessarily to the same aspect, and they mean at least one. Also, in the interest of conciseness and reducing the total number of figures, a given figure may be used to illustrate the features of more than one aspect of the disclosure, and not all elements in the figure may be required for a given aspect.

DETAILED DESCRIPTION

Figure 1:
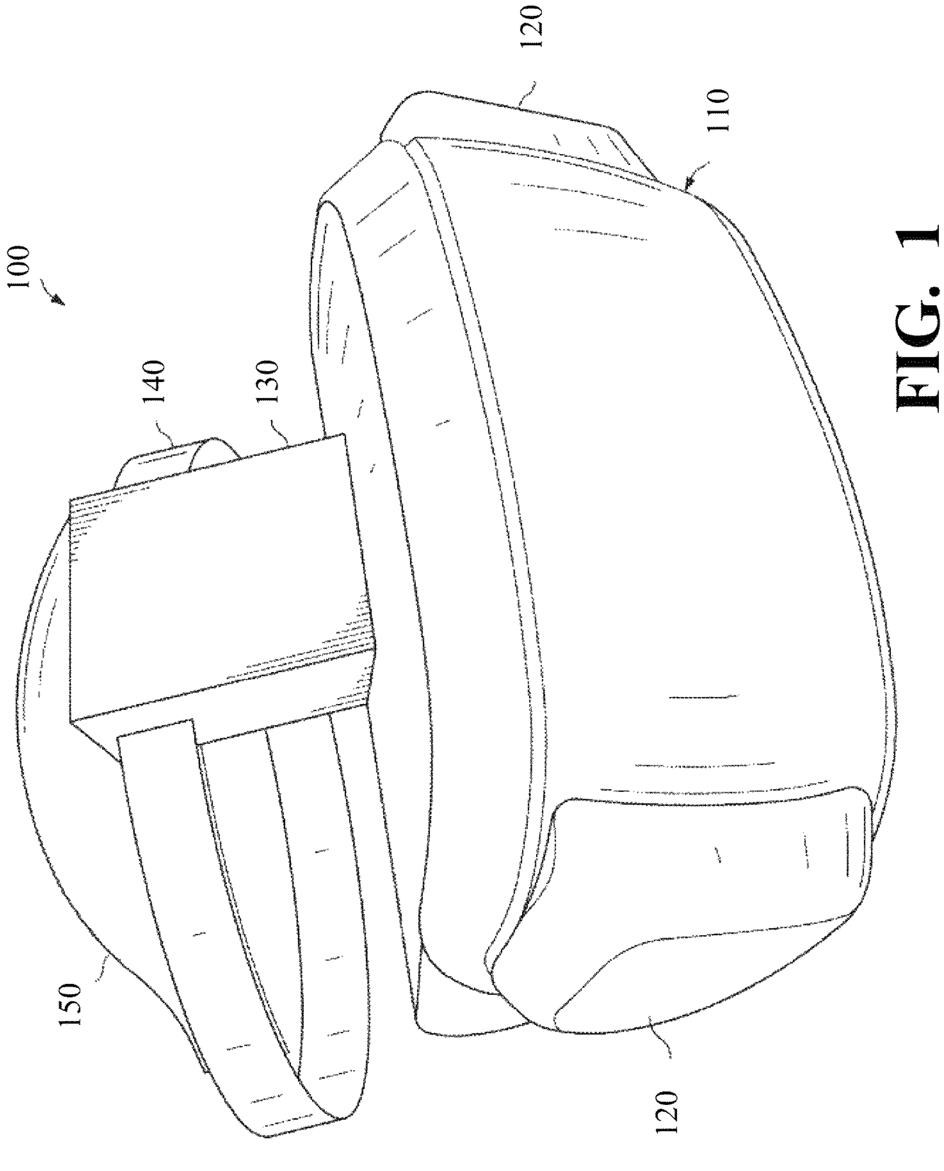
FIG. 1 is a front isometric view of an example of a headset including a display and an ophthalmic testing unit.

After an ophthalmic surgery, patients generally go home to rest and then return to the office in several days or weeks for a follow up examination. However, some surgeries may have complications, some of which may affect vision if not treated expeditiously. Sending patients home after surgery therefore has disadvantages, such as 1) missing near term complications that might occur several hours to days after surgery; and 2) delaying measurements of the patient's condition, such as waiting until a next regular eye appointment, which could be several months after surgery. Further complicating this, patients are sometimes unaware of post-surgical complications as they may not be actively monitoring for changes in visual performance.

Implementations of this disclosure address problems such as these by utilizing a portable headset and a companion device to monitor eyes of a patient, and to evaluate recovery of the patient, for an ophthalmic condition. For example, the recovery could be from PRK, LASEK, refractive lens exchange, corneal transplants, glaucoma, retinal detachment, or vitrectomy. In some implementations, the system may include a headset configured to be worn by a user (e.g., the patient) and a device in communication with the headset. In some cases, the device may be a user device, such as a mobile device (e.g., a mobile phone, laptop, or tablet) or desktop computer. In some cases, the device may be workstation or server (e.g., a cloud based computer). The headset may include a display, such as a VR, AR, or MR display. The headset may also include an ophthalmic testing unit comprising one or more sensors (e.g., pupil detectors and/or retinal detectors). The sensors may be used to obtain sensor information indicating a physiological measurement of an eye of the user. For example, the physiological measurement could comprise a measure of visual acuity, drooping eye lids, blink pattern, blood vessels, inflammatory cells, IOP, muscle movement, corneal curvature, or pupil response.

The device may include a processor configured to execute instructions stored in a memory to perform various steps, including receiving surgical information and sensor information. For example, the device can receive the surgical information from a data structure. The surgical information may correspond to a first time in which a physiological measurement of the eye is obtained. For example, the surgical information may correspond to a condition of the eye in connection with the PRK, LASEK, refractive lens exchange, corneal transplants, glaucoma, retinal detachment, or vitrectomy. The device can also receive the sensor information from the headset. In some cases, the device can periodically receive updates of the sensor information from the headset. The sensor information may correspond to a second time in which a physiological measurement is obtained via the headset. The device can then generate an ophthalmic score based on a comparison between the surgical information and the sensor information. The device can also generate an alert, and in some cases, a recommendation, based on the ophthalmic score. As a result, eyes of the user can be monitored and evaluated following an ophthalmic surgery to detect various post-surgical symptoms and/or complications.

In some implementations, a system may utilize the headset to monitor and measure a patient's eye health following ophthalmic surgical procedures. The headset may comprise a diagnostic/monitoring headset system that is portable to enable the user to take and run tests themselves (e.g., self-administer at home) or with the help of another without requiring significant technical training. The headset may connect to a user device, such as a laptop or small desktop computer, to connect to a network to transmit and receive information (e.g., receive a test to perform and/or transmit sensor information). In some cases, the headset may be configured to connect directly to the network (e.g., without the user device). Tests performed by the ophthalmic testing unit may include: 1. a visual acuity test (e.g., the headset can periodically perform a visual acuity test of the user to see if their vision is deteriorating or not improving at a rate that it should post-surgery); 2. ptosis monitoring (e.g., the headset can examine the user for drooping eyelids, which might indicate additional complications); 3. a dry eye disease test (e.g., the headset can image tear break up time and/or sense blink patterns to assess dry eyes to measure and track dry eye complications); 4. a vascularization of blood vessels test (e.g., the headset can detect and track the appearance of blood vessels in the cornea, which may indicate an infection of the eye); 5. an irritation of blood vessels test (e.g., the headset can detect blood vessels that are irritated in the user's eyes, such as bloodshot eyes, which could be used in conjunction with other measurements to determine if a surgical complication is present); 6. a cell flare test (e.g., the headset can monitor for individual inflammatory cells or proteins that have leaked from blood vessels to determine the emergence of a surgical complication); 7. a visual field test (e.g., the headset can detect a change or deterioration in the visual field of the patient which may be caused from a surgery, for example, due to high IOP, and which may call for intervention to prevent visual field loss); 8. an eye muscle movement test (e.g., the headset can measuring eye muscle movement to monitor the healing of a surgery that has impacted intraocular muscles); 9. a corneal topography test (e.g., the headset can monitor for unexpected changes in the corneal curvature by examining glint reflections 10. a pupil response test (e.g., the headset can perform a pupil response test to monitor neurological complications or damage to the optic nerve); 11. a contrast test (e.g., the headset can perform a contrast test to determine how well an intraocular lens (IOL) implantation may have improved contrast, which may also be in conjunction with a cell flare test to determine presence of an infection); 12. a retina thickness test (e.g., a retina detector of the headset 100 (e.g., the ophthalmic testing unit 1024) can perform a retinal OCT a-scan, or b-scan, which may be compared to data collected in office to determine the development of retinal edema).

In some implementations, the headset may be an optical diagnostic headset. The headset can utilize VR to monitor eye health post ophthalmic surgery by testing, exercising, and imaging the eyes at frequent time intervals. In some implementations, data from frequent testing via the headset may be sent to via a network (e.g., Wi-Fi) to a system device downstream to enable utilization by an ophthalmologist or clinical staff for diagnosis. For example, the system device, receiving the sensor information, may enable the ophthalmologist to call the user back if abnormal results are detected (e.g., exceeding a range for a given ophthalmic condition). In some implementations, a machine learning model can be trained to determine specific symptoms and/or trends from the data which can trigger an alert (e.g., transmitted via the network to the system device utilized by the clinical staff).

These descriptions are provided for exemplary purposes only and should not be considered to limit the scope of the headset periocular temperature and humidity control unit. Certain features may be added, removed, or modified without departing from the spirit of the claimed subject matter.

FIG. 1 is a front isometric view of an example of a headset 100 including an ophthalmic testing unit. In the example shown, the headset 100 includes a display housing 110, sensor housings 120, a head strap attachment 130, a head strap 140, and a forehead rest 150. In some implementations, the headset 100 may comprise a VR headset. In the illustrated implementation, the sensor housings 120 are coupled to a right and left side of the display housing 110. The sensor housings 120 can be housings for cameras or other optical detection devices, for example. In some implementations, the sensor housings 120 may include one or more temperature and/or humidity sensors. In some implementations, the sensor housings 120 may be in communication with a periocular space within the headset 100 such that one or more sensors (e.g., humidity, temperature sensors) are configured to measure air conditions (e.g., humidity, temperature) of the periocular space within the headset 100. In other implementations, one or both of the sensor housings 120, or one or more components of the sensor housings 120, may be positioned on the front of the display housing 110, on a top surface of the display housing 110, on a bottom surface of the display housing 110, and/or on the head strap 140. In some implementations, the headset 100 does not include sensor housings 120 coupled to an exterior of the headset 100. In that regard, electronic components positioned within the sensor housings 120 could be positioned within one or more components of the headset 100, such as the display housing 110, or the head strap 140.

Figure 2:
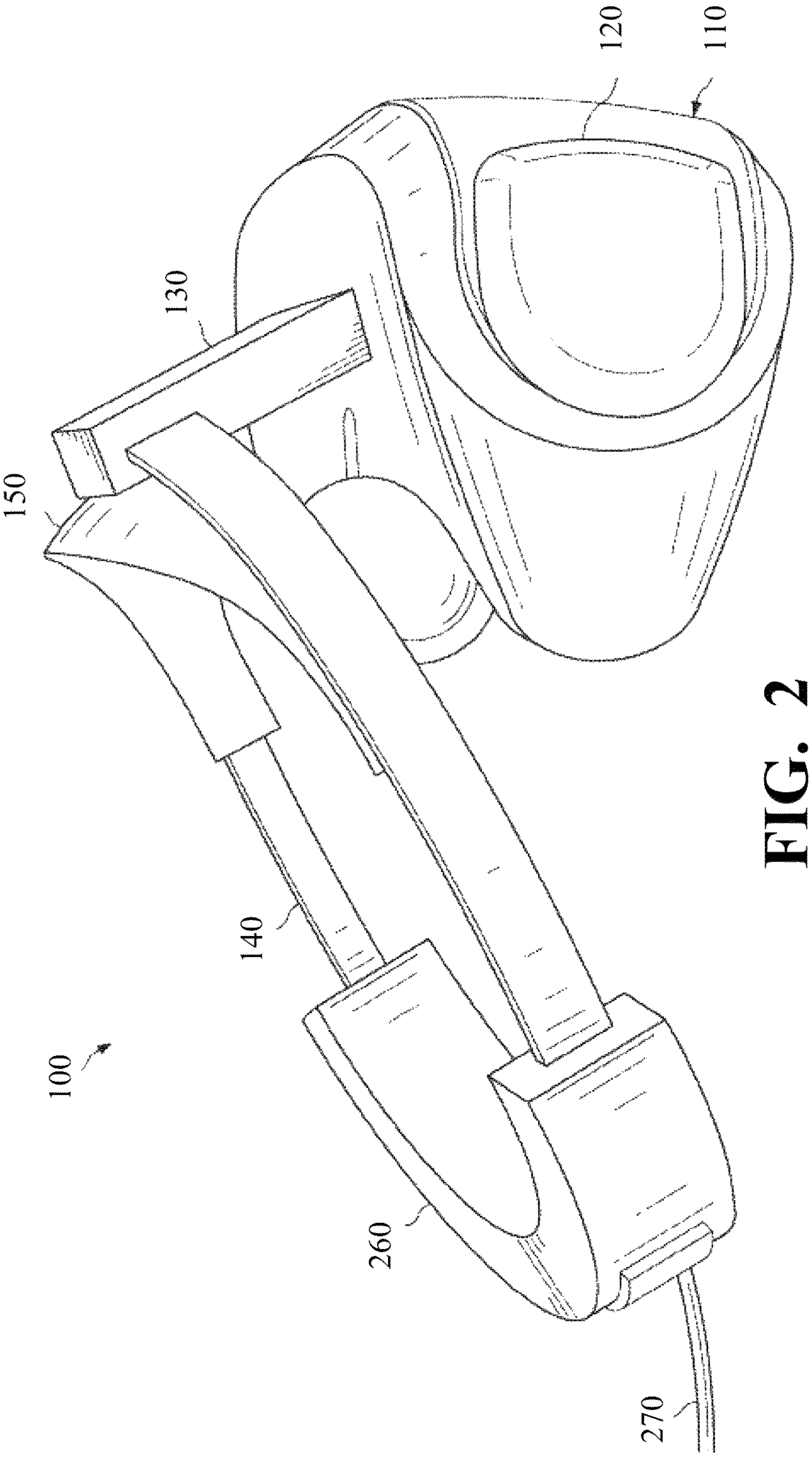
FIG. 2 is a side view of an example of a headset incorporating including a display and an ophthalmic testing unit.

FIG. 2 is a side view of an example of the headset 100. In the example shown, the headset 100 includes a head strap tightener or tension adjuster 260 and a power cord 270. Also visible are the display housing 110, sensor housing 120, head strap attachment 130, head strap 140, and forehead rest 150. It will be understood that, in some implementations, the headset 100 does not include the power cord 270, but rather includes a battery coupled to the headset 100 and configured to provide electrical power to the components of the headset 100.

Figure 3:
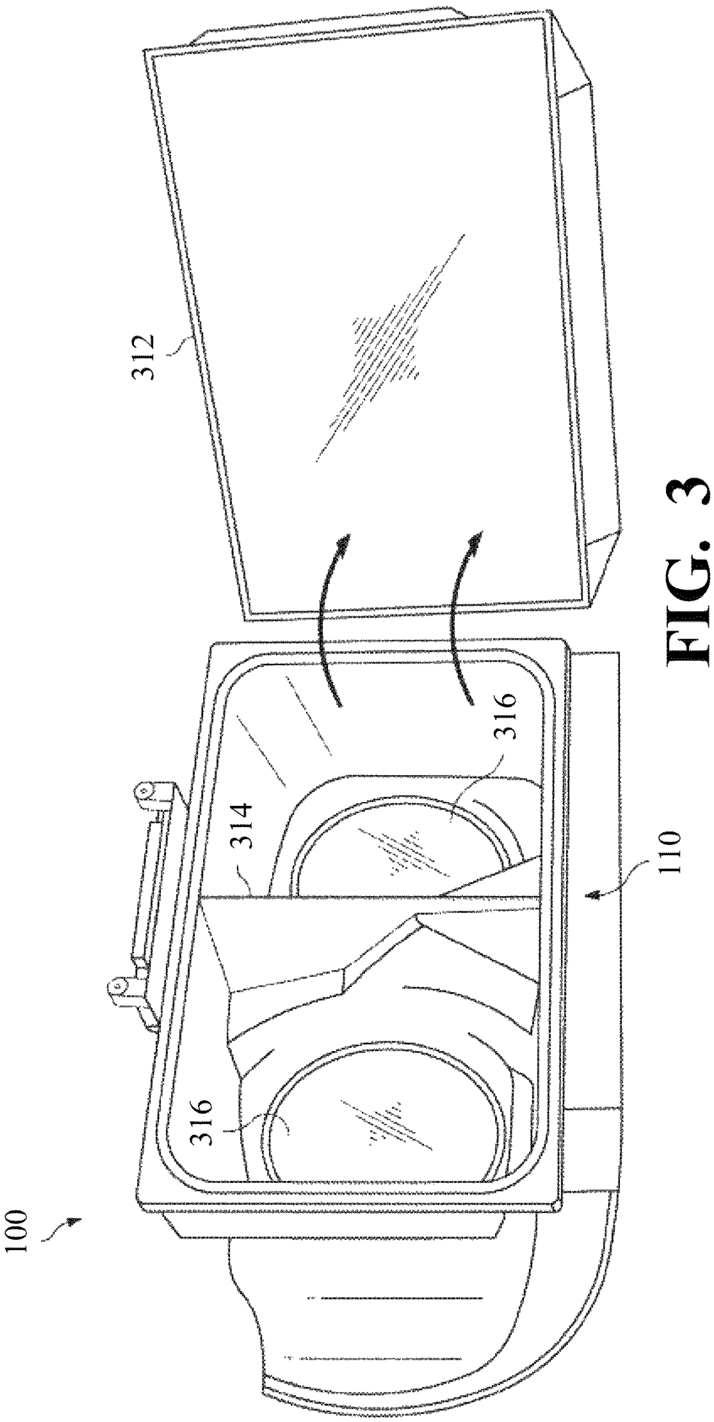
FIG. 3 is an exploded view of a portion of an example of a headset including a display and a display and an ophthalmic testing unit.

FIG. 3 is an exploded view of a portion of the headset 100 in accordance with at least one implementation of the present disclosure. For example, FIG. 3 shows an exploded view of a display housing of a headset 100, such as the display housing 110. Shown is a display 312, which attaches to the display housing 110. Also shown is a divider 314 separating the display view between the user's eyes. In an example, the display 312 shows an image through one lens 316, and a slightly different image through the other lens 316, such that the user perceives a 3D image. In an example, the headset may also be used to display 2D images, or to display images only to one eye at a time. In other implementations, the headset 100 does not include the divider 314 and/or the lenses 316.

As explained further below, in some implementations, the display 312 is configured to display images to the patient or subject while the headset 100 is performing a protocol to test for ophthalmic conditions. In some aspects, the headset 100 can include a periocular temperature and humidity control unit as shown in FIGS. 1 and 2. In some aspects, the display can be used to condition or induce stress in the eye to facilitate testing.

Figure 4:
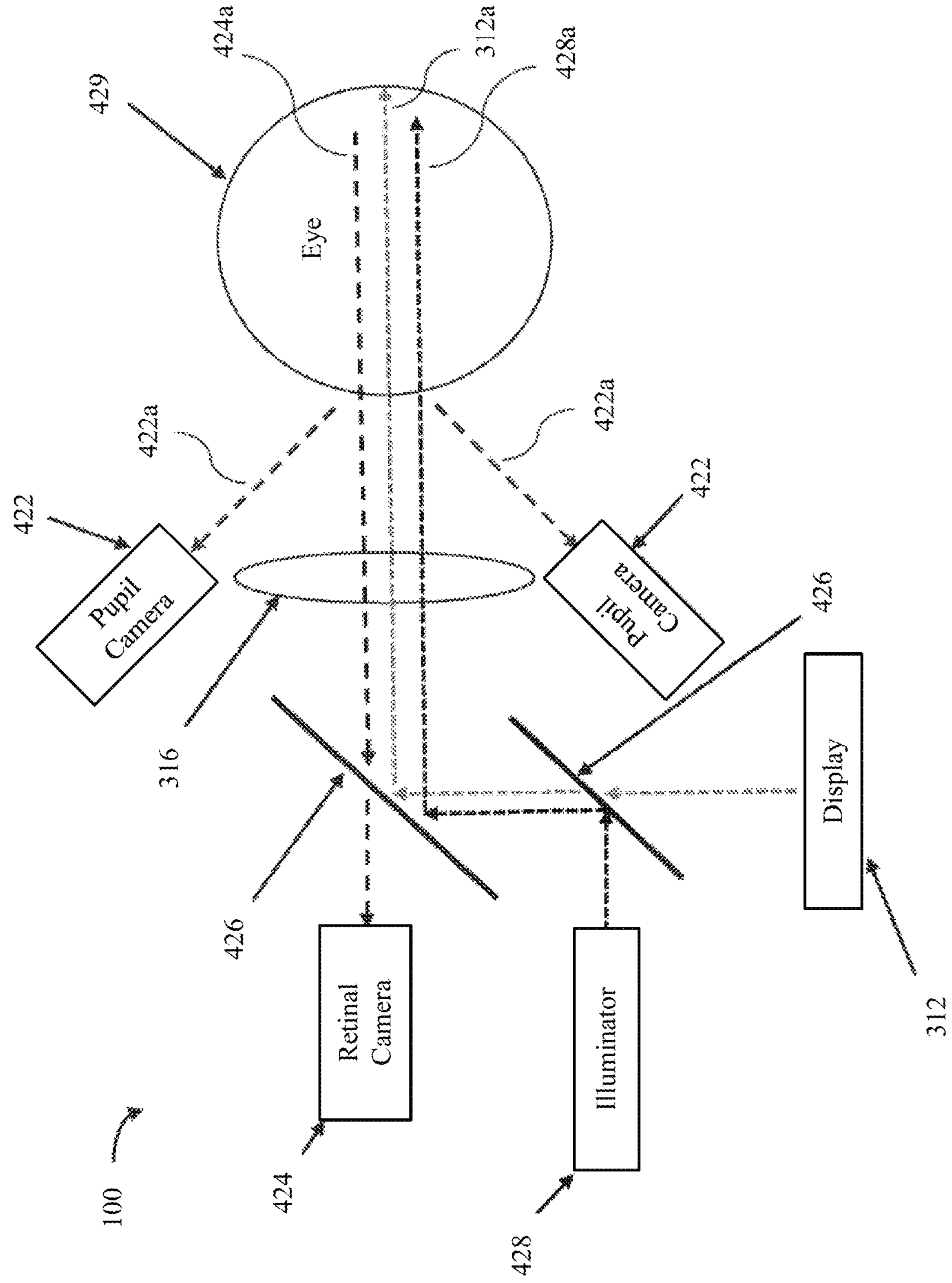
FIG. 4 is a diagrammatic representation of light paths within an exemplary headset that includes a display and an ophthalmic testing unit.

FIG. 4 is a diagrammatic representation of an optical configuration of an ophthalmic testing unit within the headset 100 for diagnosing and/or grading ophthalmic conditions, according to a first implementation shown by way of example. In that regard, the ophthalmic testing unit shown in FIG. 4 is configured to obtain one or more physiological measurements of an eye, for example, blink rate, frequency, or pattern, blink duration, blink speed or slope, the size/brightness/location of reflections on the surface of the eye, and/or the thickness of the tear film of the eye, including any meniscus and convexity formed at the edge of the eyelid. Other examples may include a measure of visual acuity, drooping eye lids, blood vessels, inflammatory cells, IOP, muscle movement, corneal curvature, or pupil response. In this first implementation shown in FIG. 4, the pupil detectors 422 are beside the eyepiece lens 316. The example shown in this figure may include a same or a different configuration than shown in FIG. 3. In the example of FIG. 4, the headset 100 further includes two off-axis pupil detectors 422, a retinal detector 424, two beam splitters 426, and an illuminator 428. The pupil detectors 422 and/or the retinal detector 424 can include optical detectors, cameras, or any other suitable detector.

In this example, light 312*a* from the display 312 is not passed directly through the eyepiece lens 316, but instead passes through a first beam splitter 426 and reflects from a second beam splitter 426 before passing through the eyepiece lens 316 and into the eye 429 of the user. Light 428*a* from the illuminator 428 (e.g., infrared (IR) light) reflects from a first beam splitter 426 and a second beam splitter 426 before passing through the eyepiece lens 316 to the eye 429. The light 428*a* may be used to illuminate features on or inside the eye 429 that may be imaged or otherwise detected by the pupil detectors 422 or retinal detector 424. In this example, light 422*a* reflecting from the surface of the eye 429 passes into the pupil detectors 422 without first passing through any other optical components. However, Light 424 a reflecting from the back of the eye passes through the eyepiece lens 316 and a beam splitter 426 before entering the retinal detector 424. In some implementations, the display 312 could be passed directly through the eyepiece lens 316. For example, the display 312 could be configured directly behind the eyepiece lens 316 with or without utilizing beam splitters. Additionally, in some implementations, the illuminator 428 may be configured beside the eyepiece lens 316 (e.g., on axes like the pupil detectors 422) instead of behind the eyepiece lens 316 (e.g., with or without utilizing beam splitters).

In some implementations, the pupil detectors 422 may observe other parts of the eye, including but not limited to the eyelids, eyelashes, cornea, IOL, corneal tear film, tear ducts, and Meibomian glands, instead of or in addition to the pupil. In some implementations, other arrangements of optical components (e.g., illuminators, cameras, beam splitters, and lenses) may be used to achieve the effects disclosed herein.

Figure 5:
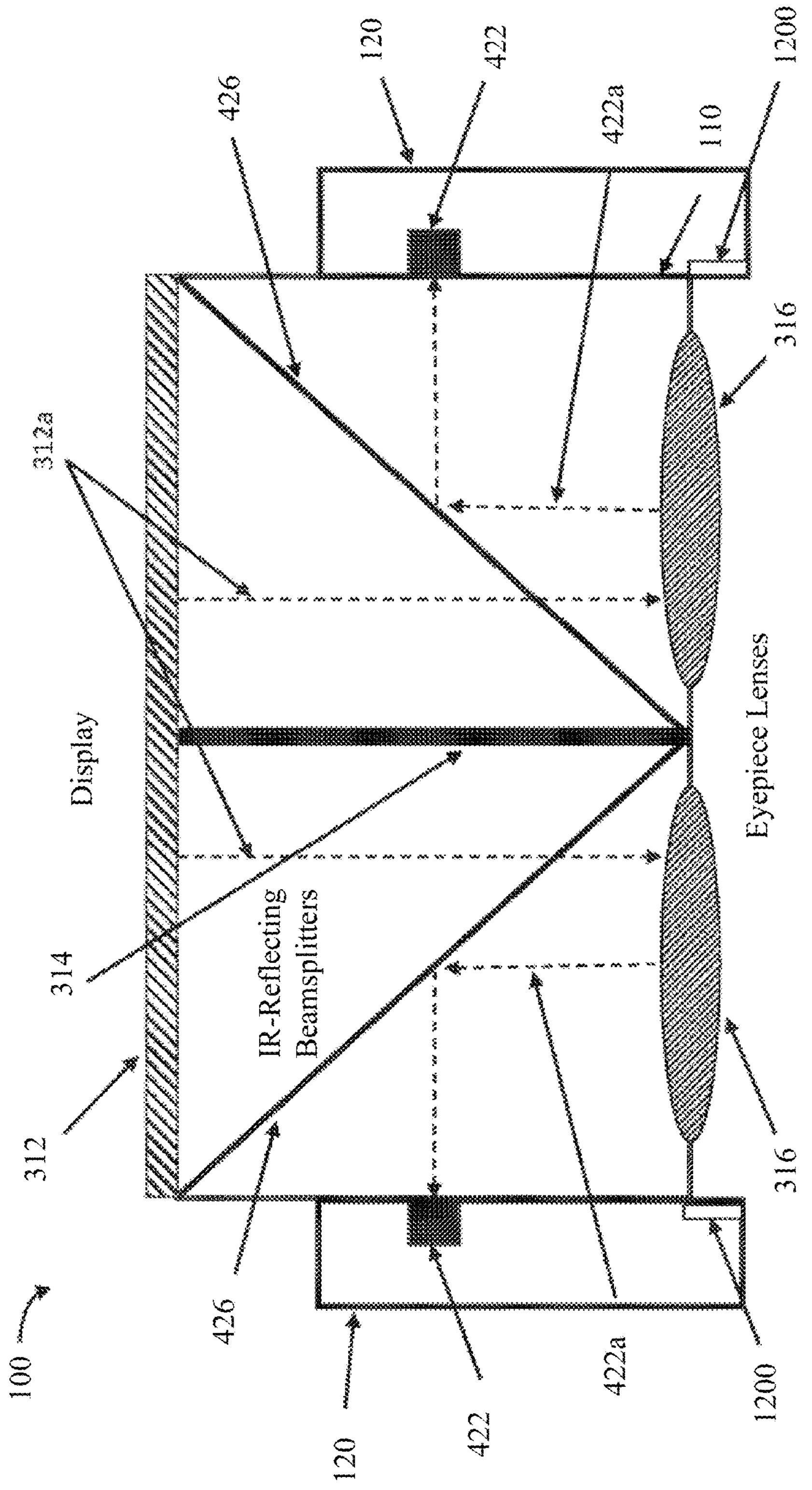
FIG. 5 is another diagrammatic representation of light paths within an exemplary headset that includes a display and an ophthalmic testing unit.

FIG. 5 is a diagrammatic representation of light paths within the headset 100 according to a second implementation shown by way of example. In this example, the display 312, divider 314, two eyepiece lenses 316, and two beam splitters 426 are situated within the display housing 110. The divider 314 defines two separate regions of the display 312. Each portion of the display emits light 312*a* (e.g., an image) that passes through a beam splitter 426 and through an eyepiece lens 316. Light 422*a* from the illuminator 428 reflecting from the surface of each eye passes through an eyepiece lens 316, reflects from a beam splitter 426, and into a pupil camera 422, which sits within a sensor housing 120. In this second implementation shown in FIG. 5, the pupil detectors 422 are behind the eyepiece lens 316. The source of light 422*a* which reflects from the surface of the eye may include one or more illuminators, such as infrared (IR) illuminators 428 (see FIGS. 4, 7A, 7B). In the implementation shown in FIG. 5, the beam splitter 426 reflects IR light but does not reflect visible light, such as light provided by the display 312. In other implementations, such as the implementation shown in FIG. 4, the beam splitters 426 reflect IR light and additional light, such as visible light.

In some implementations, periocular temperature and humidity controller circuit boards 1200 may be located within the sensor housings 120. The temperature and humidity controller circuit boards 1200 may comprise one or more of a humidity sensor configured to measure a humidity within the periocular space of the headset 100, a temperature sensor configured to measure a temperature within the periocular space of the headset 100, a dehumidifier or humidity control element configured to control or adjust the humidity within the periocular space of the headset 100, a heating element, and/or a cooling element. Although more than one temperature and humidity controller circuit boards 1200 are shown in FIG. 5, the headset 100 can include a single temperature and humidity controller circuit board, or multiple temperature and humidity controller circuit boards. Further, in some implementations, the headset can include one or more temperature and/or humidity sensors in communication with the temperature and humidity controller circuit boards 1200 and configured to monitor a temperature and/or a humidity in the external environment around the headset 100.

Figure 6:
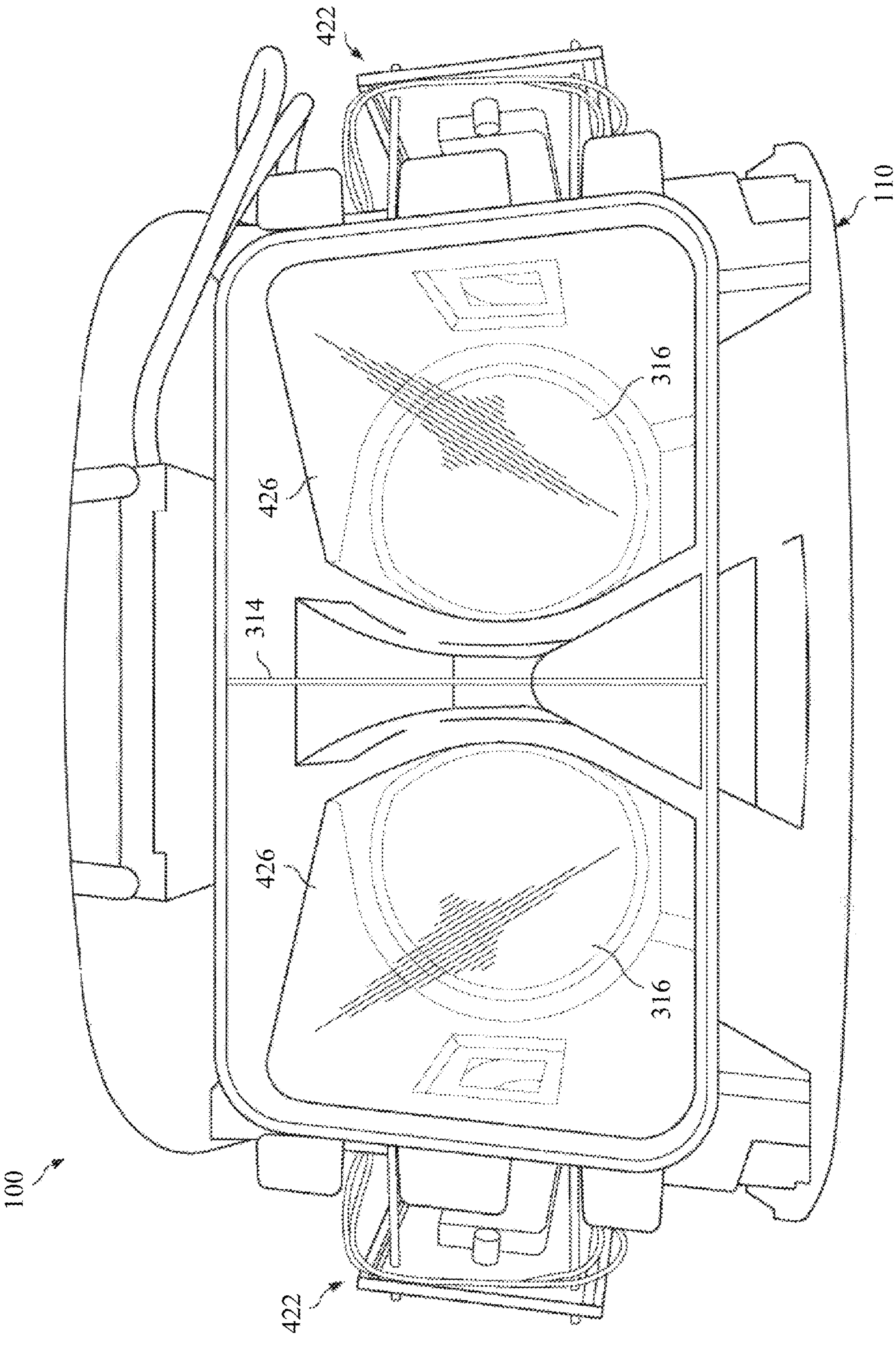
FIG. 6 is a front cutaway view showing exemplary optical components in an exemplary that includes a display and an ophthalmic testing unit.

FIG. 6 is a front view of a portion of the headset 100 including the ophthalmic testing unit in accordance with at least one implementation of the present disclosure. For clarity, the display 312 has been removed from this view. Visible are the display housing 110, divider 314, two eyepiece lenses 316, two pupil detectors 422, and two beam splitters 426.

Figure 7A:
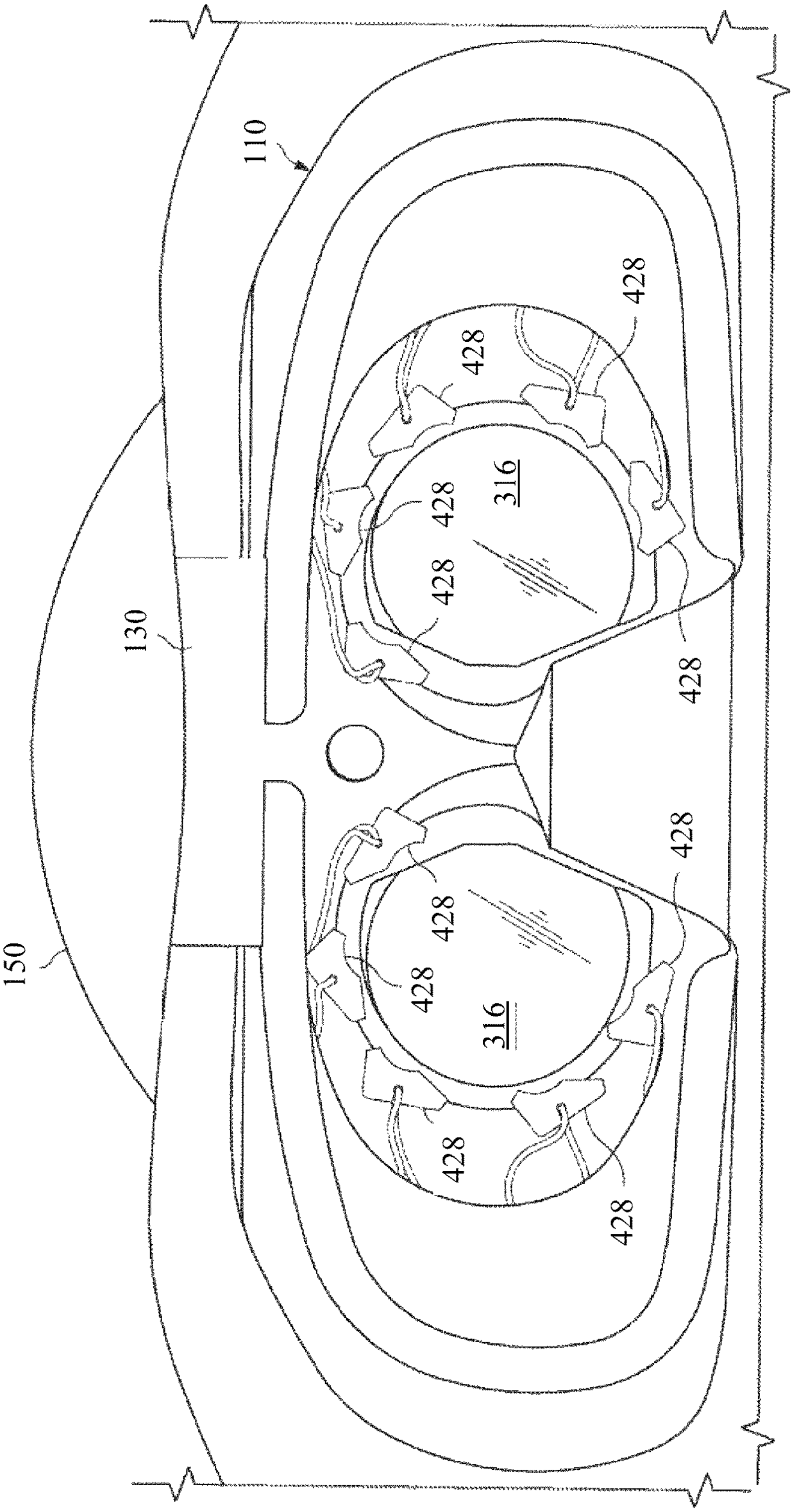
FIG. 7A is a rear view of a portion of an exemplary headset that includes a display and an ophthalmic testing unit.
Figure 7B:
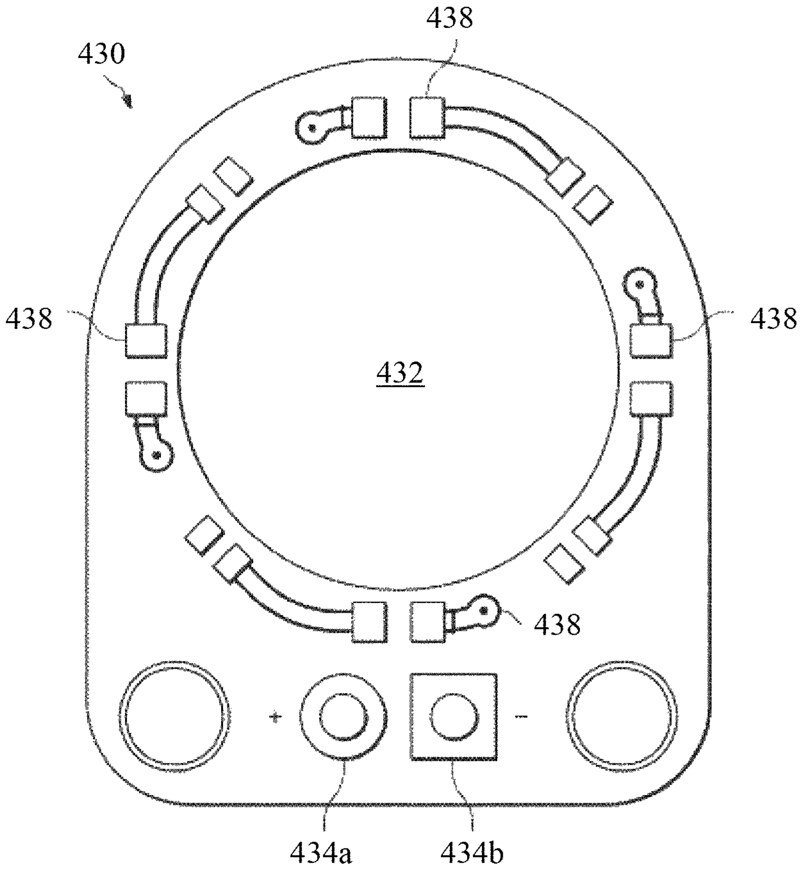
FIG. 7B is a front view of an example of an illuminator assembly for an ophthalmic testing unit for a headset.

FIG. 7A is a rear view of a portion of the headset 100 in accordance with at least one implementation of the present disclosure. Visible are the display housing 110, head strap attachment 130, forehead rest 150, and eyepiece lenses 316. Surrounding each eyepiece lens 316 is a plurality of illuminators 428 (e.g., infrared LEDs) that are configured to illuminate the eye for observation by the pupil detectors 422 and/or retinal cameras 424. FIG. 7B shows an illuminator assembly 430, according to an implementation of the present disclosure. In that regard, the illuminator assembly includes a plurality of illuminators 438 (e.g., infrared LEDs), a positive power connector 434*a*, a negative power connector 434*b*, and an aperture or opening 432. In some implementations, the aperture 432 is positioned around a camera of an ophthalmic testing unit.

Figure 8:
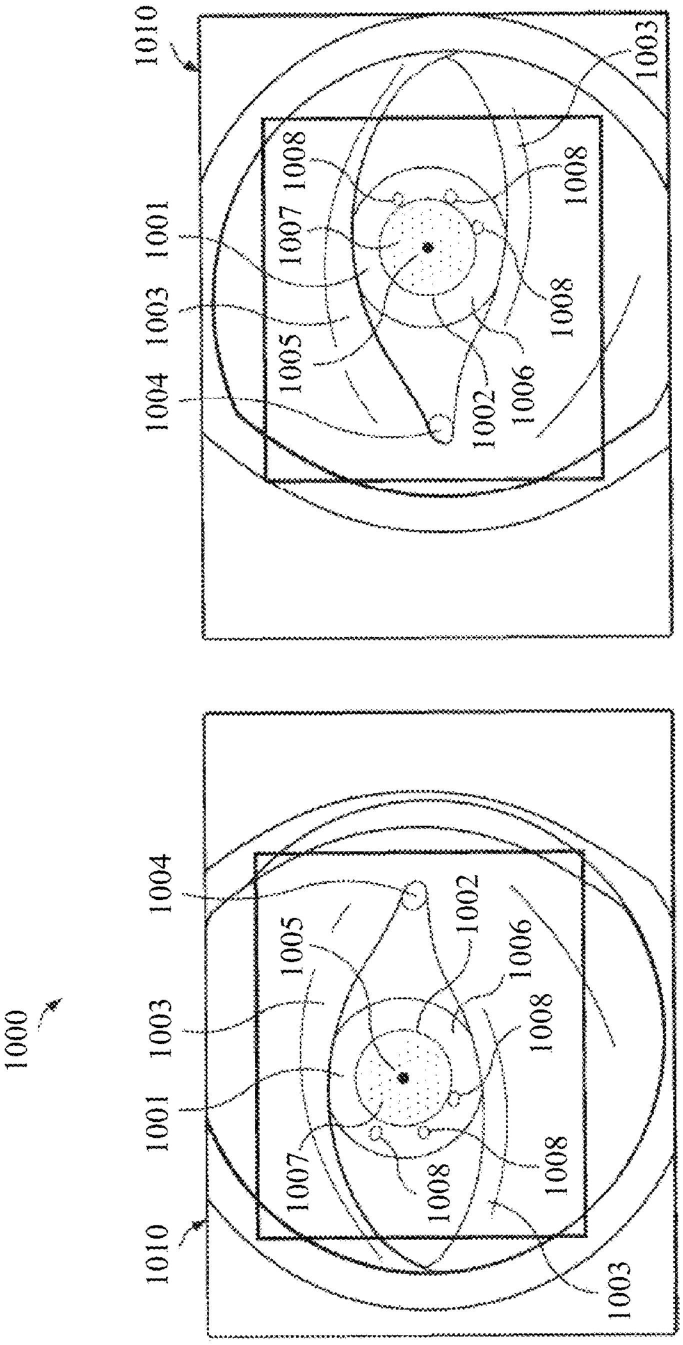
FIG. 8 is an exemplary pair of pupil camera images from a headset that includes a display and an ophthalmic testing unit.

FIG. 8 is an exemplary view of a graphical interface for testing or grading ophthalmic conditions, such as for determining an ophthalmic score. The interface 1000 shows a pair of pupil camera images 1010 from a headset 100 in accordance with at least one implementation of the present disclosure. Visible are corneal tear film 1001, pupil 1002, eyelids 1003, tear ducts 1004, corneas 1006, intraocular lenses 1007, reflections 1008, and computer-generated gaze indicators 1005 at the center of each pupil 1002. In some aspects, the reflections 1008 may represent glints from the illuminators 428. For example, for a dry test, various features of this image may be used to assess the hydration or dryness of the eyes, including but not limited to blink pattern, blink rate or frequency, blink duration, between-blink interval, blink speed or slope, the size/brightness/location of reflections 1008 on the surface of the eye, and direct observation and measurement (e.g., pixel count and rate of change) of the thickness of the corneal tear film 1001, including any meniscus and convexity formed at the edge of the eyelid. In other aspects, other features of this image may be used to assess other ophthalmic conditions.

Figure 9:
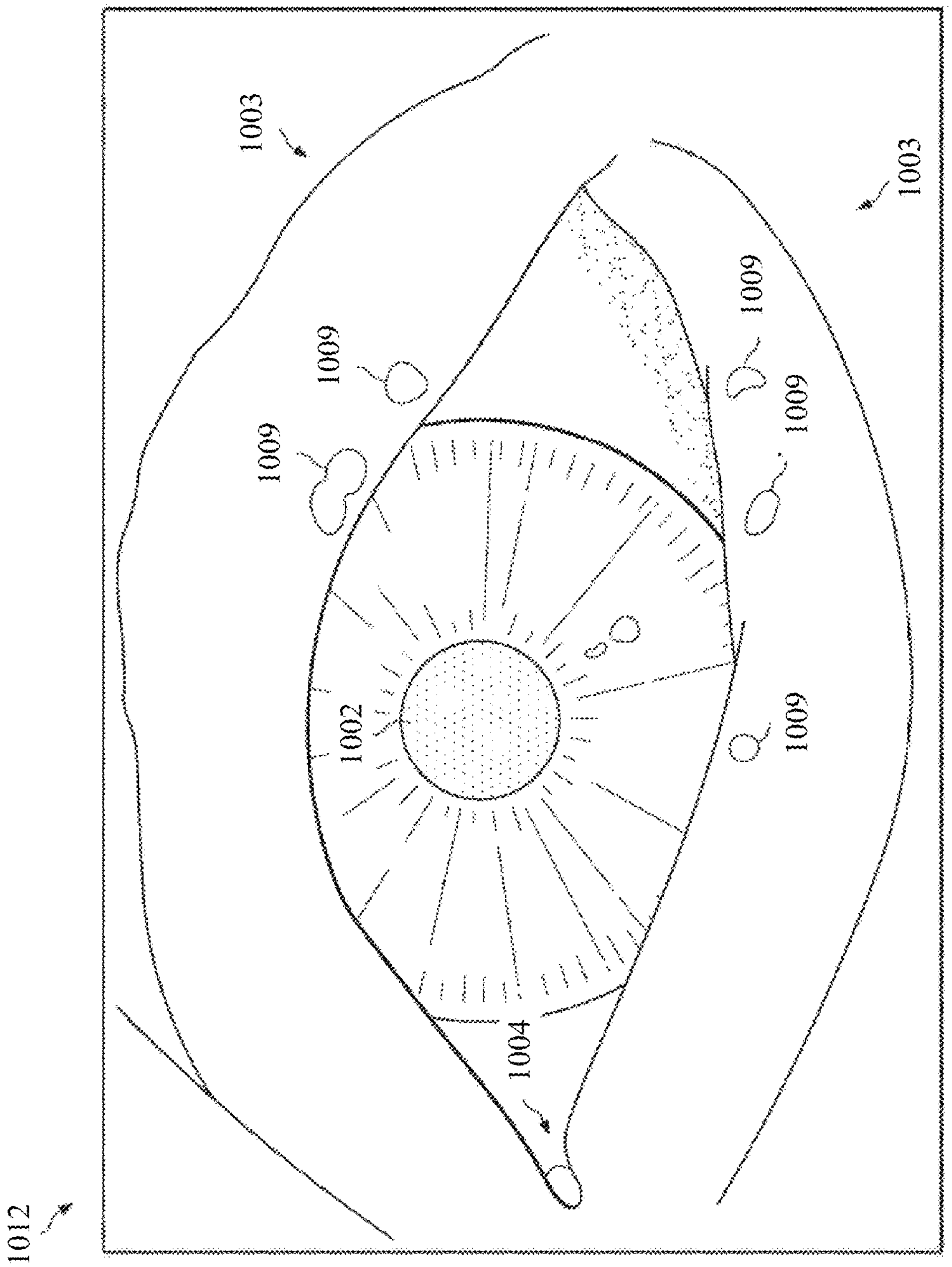
FIG. 9 is an exemplary pupil camera image from a headset that includes a display and an ophthalmic testing unit.

FIG. 9 is an exemplary pupil camera image 1012 from the headset 100 in accordance with at least one implementation of the present disclosure. Visible are the pupil 1002, eyelids 1003, and tear duct 1004. In this example, the user has been asked, via output to display of the headset, to manually pull open their eyelids 1003, revealing Meibomian glands 1009. For example, irregularities in the Meibomian glands or tear duct may be indicative of both the existence and potential causes of a dry eye problem. Thus, images of the Meibomian glands may be extremely useful in the process of determining a diagnosis and treatment. In other aspects, the user may be asked via the headset to assist with other measurements. In addition to automated analysis, such pupil camera images 1000 may be communicated to one or more clinicians, either co-located with the headset and the device or in one or more remote locations.

Figure 10:
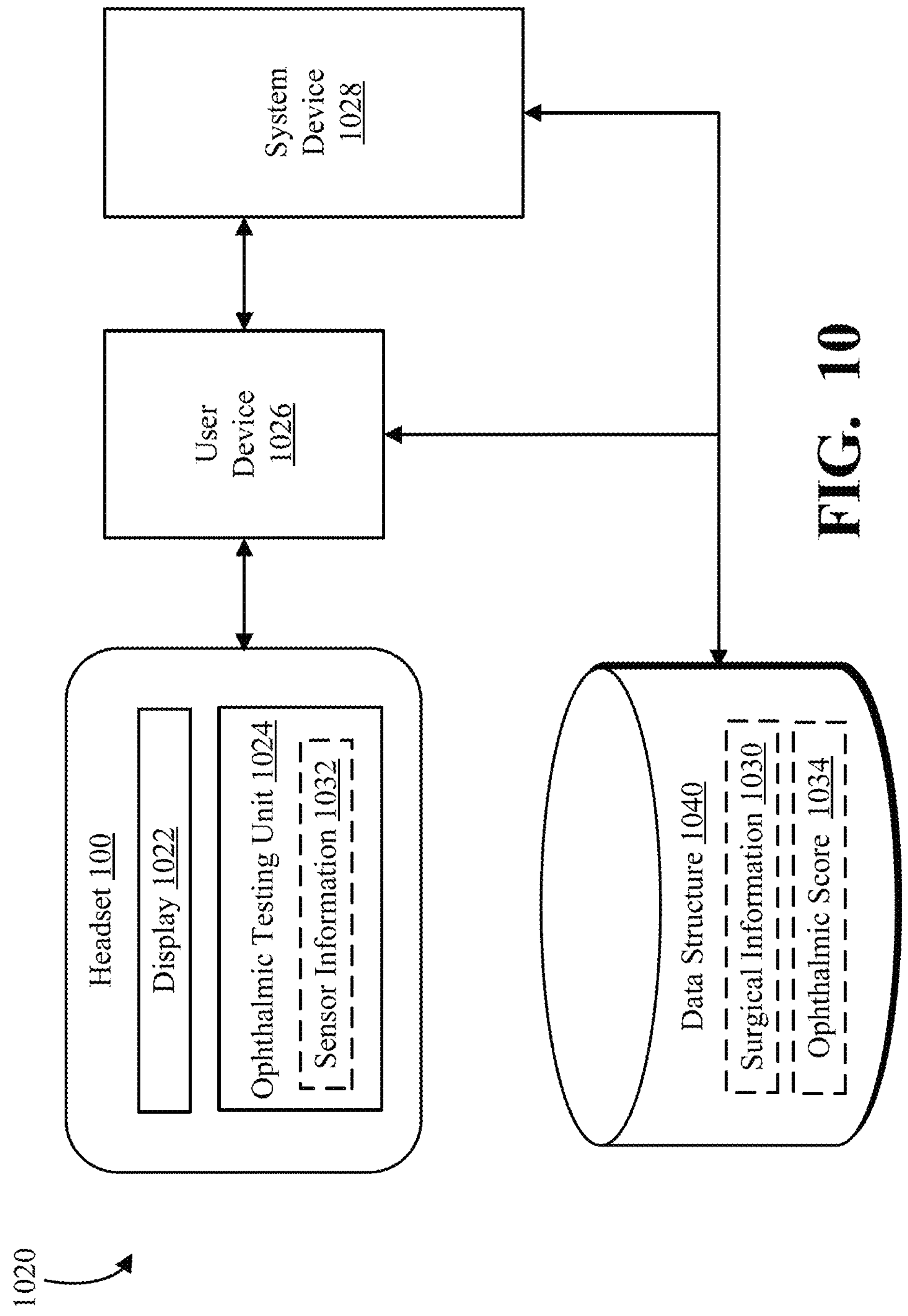
FIG. 10 is an example of a system for monitoring ophthalmic conditions using a headset.

FIG. 10 is an example of a system 1020 for monitoring ophthalmic conditions using the headset 100. For example, the headset 100 may include a display 1022 and an ophthalmic testing unit 1024, such as the display and ophthalmic testing unit described above with respect to FIGS. 1-9. The system 1020 may also include a device in communication with the headset 100, such as a user device 1026 and/or a system device 1028. For example, the user device 1026 may be a mobile device (e.g., a mobile phone, laptop, or tablet) or desktop computer utilized by the user. In another example, the system device 1028 may be workstation or server (e.g., a cloud based computer) utilized by clinical staff. The headset 100 may utilize the display 1022 to generate VR, AR, or MR for the user. The headset 100 may also utilize the ophthalmic testing unit 1024 to obtain sensor information from the user. The ophthalmic testing unit 1024 may utilize the sensors described herein (e.g., the pupil detectors 422 and the retinal detector 424) to obtain sensor information indicating one or more physiological measurements of one or more eyes of the user. For example, a physiological measurement could comprise a measure of visual acuity, drooping eye lids, blink pattern, blood vessels, inflammatory cells, IOP, muscle movement, corneal curvature, or pupil response.

The user device 1026 may communicate with the headset 100. For example, the user device 1026 may run an application program (e.g., an app) to wirelessly control the headset 100, including for testing, monitoring, and evaluating performed utilizing the display 1022 and the ophthalmic testing unit 1024. Additionally, the user device 1026 may connect to a network to communicate with the system device 1028. However, in some implementations, the system device 1028 might not be present, and in other implementations, the user device 1028 might not be present. For example, in some implementations, the system device 1028 may communicate directly with the headset 100, through a network, without the user device 1026.

The user device 1026 and/or the system device 1028 may include a processor configured to execute instructions stored in a memory to perform various steps, including receiving surgical information 1030 and receiving sensor information 1032. The user device 1026 and/or the system device 1028 can receive the surgical information 1030 from a data structure 1040 (e.g., a database). The surgical information 1030 may correspond to a first time in which a physiological measurement of one or more eyes of the user is obtained. For example, the surgical information 1030 may correspond to a surgical condition of the eye, such as in connection with PRK, LASEK, refractive lens exchange, corneal transplants, glaucoma, retinal detachment, or vitrectomy.

The user device 1026 and/or the system device 1028 can also receive the sensor information 1032 from the headset 100. In some cases, the user device 1026 and/or the system device 1028 can periodically receive updates of the sensor information 1032 (e.g., every N hours every, where N is an integer value). The sensor information 1032 may correspond to a second time in which a physiological measurement of the one or more eyes of the user is obtained (e.g., some amount of time after the first time, such as hours or days later). The user device 1026 and/or the system device 1028 can generate an ophthalmic score 1034, based on a comparison between the surgical information 1030 and the sensor information 1032. For example, the ophthalmic score 1034 may represent a post-surgical evaluation of the surgical recovery that may be monitored by the user and/or clinical staff. As a result, the one or more eyes of the user can be monitored and evaluated following an ophthalmic surgery to detect various post-surgical symptoms and/or complications.

In various implementations, the headset 100 may perform one or more tests, singly or in series, via the display 1022 and the ophthalmic testing unit 1024. For example, the tests may include: 1. a visual acuity test (e.g., the headset 100 can periodically perform a visual acuity test of the user to see if their vision is deteriorating or not improving at a rate that it should post-surgery); 2. ptosis monitoring (e.g., the headset 100 can examine the user for drooping eyelids, which might indicate additional complications); 3. a dry eye disease test (e.g., the headset 100 can image tear break up time and/or sense blink patterns to assess dry eyes to measure and track dry eye complications); 4. a vascularization of blood vessels test (e.g., the headset 100 can detect and track the appearance of blood vessels in the cornea, which may indicate an infection of the eye); 5. an irritation of blood vessels test (e.g., the headset 100 can detect blood vessels that are irritated in the user's eyes, such as bloodshot eyes, which could be used in conjunction with other measurements to determine if a surgical complication is present); 6. a cell flare test (e.g., the headset 100 can monitor for individual inflammatory cells or proteins that have leaked from blood vessels to determine the emergence of a surgical complication); 7. a visual field test (e.g., the headset 100 can detect a change or deterioration in the visual field of the patient which may be caused from a surgery, for example, due to high IOP, and which may call for intervention to prevent visual field loss); 8. an eye muscle movement test (e.g., the headset 100 can measuring eye muscle movement to monitor the healing of a surgery that has impacted intraocular muscles); 9. a corneal topography test (e.g., the headset 100 can monitor for unexpected changes in the corneal curvature by examining glint reflections 10. a pupil response test (e.g., the headset 100 can perform a pupil response test to monitor neurological complications or damage to the optic nerve); 11. a contrast test (e.g., the headset 100 can perform a contrast test to determine how well an IOL implantation may have improved contrast, which may also be in conjunction with a cell flare test to determine presence of an infection); 12. a retina thickness test (e.g., the retina detector of the headset 100 can perform a retinal OCT a-scan, or b-scan, which may be compared to data collected in office to determine the development of retinal edema).

The headset 100 is portable so that the user can advantageously take the headset 100 home post-surgery. In some cases, the user can also receive the user device 1026, configured to operate with the headset 100, and in other cases, the user may configure their own device as the user device 1026. By way of example, to look for symptoms of dry eye/irrigation, the user can wear the headset 100 and periodically, e.g., every N hours, use the headset 100 to perform a dry eye disease test that measures blink frequencies, intervals between blinks and length of blinks. In some cases, this data (e.g., the sensor information 1032) may trigger an alert and/or a recommendation for user action, such as suggesting eye drops, rest, or a return to the office for clinical examination. In some cases, alerting test results may also prompt clinical staff (e.g., via output to the system device 1028) to contact the user (e.g., via output to the headset 100 and/or the user device 1026) to perform further tests via the headset 100 and/or to return for clinical examination.

In some implementations, the headset 100 can be used to measure curvature of the eye or changes in inflammation, such as to perform a corneal topography test, e.g., every N hours. For example, the headset 100 can perform the corneal topography test by turning on various LEDs (e.g., the plurality of illuminators 438) and marking the position of their reflections, or the glints on the eyes. The data (e.g., the sensor information 1032) may be sent, for example, to the clinical staff (e.g., via output to the system device 1028) for further investigation and/or monitoring. In some implementations, to measure loss of vision or symptoms of glaucoma, the headset 100 can be used to perform a visual field test can, e.g., every N hours, after surgery. For example, the visual field test could be a Goldmann or Humphrey visual field test. In some implementations, the headset 100 can be used to perform a ptosis test to measure drooping eyelids post-surgery. This test, and others, can be combined with any of the other tests described herein. In some implementations, the headset 100 can be used to perform a contrast sensitivity test to measure the user's ability to view different contrast levels and its changes over time. The headset 100 can similarly be used to perform a test for color blindness. In some implementations, the headset 100 can be used to perform a pursuit test to monitor the ability of the eyes to track a moving object (e.g., moving the VR display). For example, the pursuit test can test speed of tracking as well as motor ability. In some implementations, the headset 100 can be used to perform a pupil response test to measure the responsiveness of each pupil. In some implementations, the headset 100 can be used to perform a visual acuity test that can be used to measure blurriness of vision or focus related symptoms. In some implementations, the headset 100 can be used to perform a spatial hyperacuity test (e.g., Amsler grid, preferential hyperacuity perimetry), such as to identify warping or distortion of the visual field. For example, this can help identify edema, neovascularization, and other distortions of the retina. Thus, the headset 100 can test for many specific symptoms in a user, in different ways, post-surgery. The headset 100 can perform the tests frequently and accurately to monitor users and to move post-ophthalmic surgery from reactive to preventative care.

In some implementations, the headset 100 may utilize the display 1022 and the ophthalmic testing unit 1024 to monitor eye health post ophthalmic surgery by exercising and by taking images of the eyes at frequent time intervals. For example, the headset 100 may be configured to exercise the eye before obtaining the sensor information 1032, such as by outputting a test pattern to the display 1022 for the eye to follow.

In some implementations, data from frequent testing via the headset 100 (e.g., the sensor information 1032) may be immediately sent via a network (e.g., Wi-Fi) to the user device 1026 and/or the system device 1028 downstream to enable utilization by the clinical staff for diagnosis. For example, the system device 1028, receiving the sensor information 1032, may enable the clinical staff to program further tests via the headset 100 and/or to call the user back if abnormal results are detected (e.g., exceeding a range for an ophthalmic condition).

In some implementations, a machine learning model can be trained to determine specific symptoms and/or trends from data, which can also trigger an alert (e.g., transmitted via the network to the system device utilized by the clinical staff). For example, the user device 1026 and/or the system device 1028 can invoke the machine learning model to determine, based on the surgical information 1030 and the sensor information 1032, recovery of the eye from an ophthalmic procedure, such as PRK, LASEK, refractive lens exchange, corneal transplants, glaucoma, retinal detachment, or vitrectomy. In another example, the user device 1026 and/or the system device 1028 can invoke the machine learning model to determine, based on the surgical information 1030 and the sensor information 1032, a symptom of the ophthalmic condition. The machine learning model may, for example, be or include one or more of a neural network (e.g., a convolutional neural network, recurrent neural network, deep neural network, or other neural network), decision tree, vector machine, Bayesian network, cluster-based system, genetic algorithm, deep learning system separate from a neural network, or other machine learning model.

Figure 11:
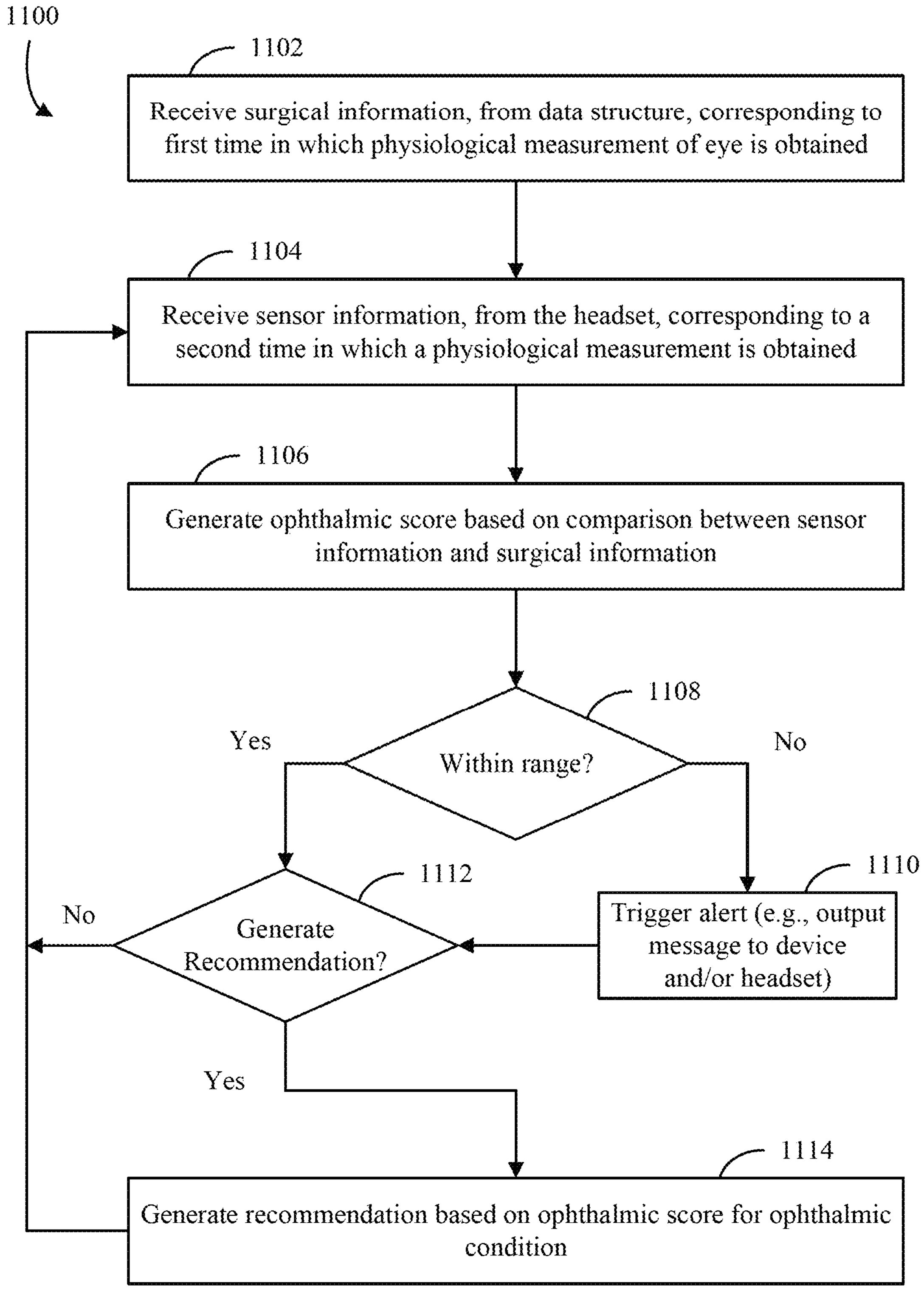
FIG. 11 is a flowchart of an example of a process for monitoring ophthalmic conditions using a headset.

FIG. 11 is a flowchart of an example of a process 1100 for monitoring ophthalmic conditions using a headset. The process 1100 can be executed using computing devices, such as the systems, hardware, and software described with respect to FIGS. 1-10. The process 1100 can be performed, for example, by executing a machine-readable program or other computer-executable instructions, such as routines, instructions, programs, or other code. The operations of the process 1100 or another technique, method, process, or algorithm described in connection with the implementations disclosed herein can be implemented directly in hardware, firmware, software executed by hardware, circuitry, or a combination thereof.

For simplicity of explanation, the process 1100 is depicted and described herein as a series of operations. However, the operations in accordance with this disclosure can occur in various orders and/or concurrently. Additionally, other operations not presented and described herein may be used. Furthermore, not all illustrated operations may be required to implement a technique in accordance with the disclosed subject matter.

At operation 1102, a device may receive surgical information, from a data structure, corresponding to a first time in which a physiological measurement of an eye of a user is obtained. The surgical information may correspond to a surgical recovery of the eye. For example, the user device 1026 and/or the system device 1028 may receive the surgical information 1030, from the data structure 1040, corresponding to a first time in which a physiological measurement of an eye of the user is obtained.

At operation 1104, the device may receive sensor information, from a headset worn by a user, corresponding to a second time in which a physiological measurement of the eye is obtained. The headset may include a display and an ophthalmic testing unit comprising one or more sensors to obtain the sensor information indicating the physiological measurement of the eye. For example, the user device 1026 and/or the system device 1028 may receive the sensor information 1032, from the headset 100, corresponding to a second time in which a physiological measurement of the eye is obtained. The headset 100 may utilize the display 1022 and the ophthalmic testing unit 1024 to obtain the sensor information 1032, including by exercising the eye before obtaining the measurement.

At operation 1106, the device (e.g., the user device 1026 and/or the system device 1028) may generate an ophthalmic score (e.g., the ophthalmic score 1034) based on a comparison between the surgical information and the sensor information. For example, the device may apply a mathematical relationship to the score, including determining whether the sensor information indicates 1) an improvement relative to the surgical information, 2) a degradation relative to the surgical information, or 3) no change relative to the surgical information. In some implementations, the ophthalmic score may represent a numerical value or percentage representing a result of the recovery.

At operation 1108, the device (e.g., the user device 1026 and/or the system device 1028) may determine whether the ophthalmic score is within a range based on the ophthalmic condition. If the ophthalmic score is within the range ("Yes"), the process 1100 may return to operation 1104 to obtain an update of the sensor information and to update the ophthalmic score for a next iteration. However, if the ophthalmic score is not within the range ("No") (e.g., the ophthalmic score exceeds the range, such as falling below a lower threshold or above an upper threshold), at operation 1110 the device may trigger an alert. For example, the alert may include outputting a message to the device (e.g., the user device 1026 to alert the user, and/or the system device 1028 to alert clinical staff) and/or the headset.

At operation 1112, the device may determine whether to generate a recommendation based on the ophthalmic score. For example, some tests and/or test results may be associated with recommendations, such as a recommendation to utilize eye drops, rest, or return to clinical staff, whereas other tests and/or test results might not. If the device determines to generate a recommendation ("Yes"), at operation 1114 the device may generate the recommendation for output (e.g., to the user device 1026 or the headset 100) based on the ophthalmic score. However, if the device determines not to generate a recommendation ("No"), the process 1100 may return to operation 1104 to obtain an update of the sensor information and to update the ophthalmic score for a next iteration.

Figure 12:
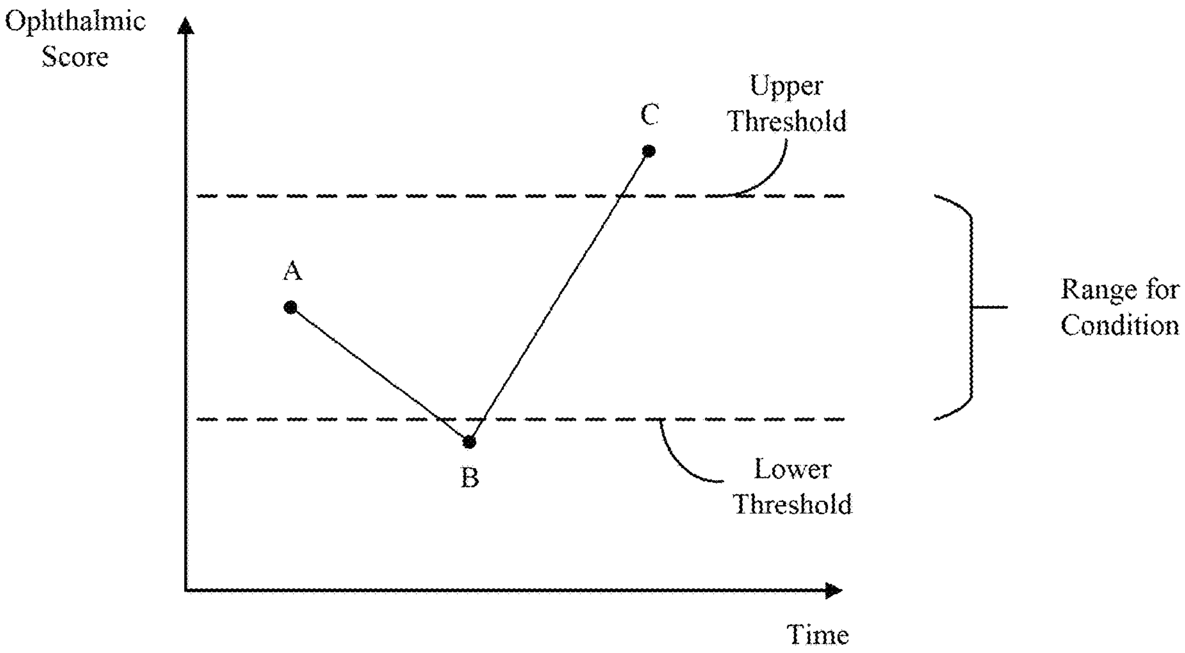
FIG. 12 is an example of monitoring ophthalmic conditions based on ophthalmic scores.

FIG. 12 is an example of monitoring ophthalmic conditions based on ophthalmic scores. For example, the user device 1026 and/or the system device 1028 may monitor recovery from an ophthalmic condition (e.g., dry eye) via the headset 100. The device may initially determine a score A (e.g., the ophthalmic score 1034) based on the surgical information and a first collection of the sensor information. In this example, the score A is within a range (e.g., between an upper threshold and a lower threshold, such as sensing the user blinking between 12 and 15 times per minute). The device may then update the sensor information (e.g., 1 hour later) to determine an update to the ophthalmic score. For example, the device may determine a score B based on the surgical information and a second collection of the sensor information (e.g., sensing the user blinking less than 12 times per minute). In this example, the score B is outside of the range, falling below a lower threshold. Further, based on the score B being less than the lower threshold, a low score alert (and a low score recommendation) may be generated. The device may then update the sensor information again (e.g., 2 hours later) to determine another update to the ophthalmic score. For example, the device may determine a score C based on the surgical information and a third collection of the sensor information (e.g., sensing the user blinking more than 15 times per minute). In this example, the score C is again outside of the range, now exceeding the upper threshold. Further, based on the score C being greater than the upper threshold, a high score alert (and a high score recommendation) may be generated.

The implementations of this disclosure can be described in terms of functional block components and various processing operations. Such functional block components can be realized by a number of hardware or software components that perform the specified functions. For example, the disclosed implementations can employ various integrated circuit components (e.g., memory elements, processing elements, logic elements, look-up tables, and the like), which can carry out a variety of functions under the control of one or more microprocessors or other control devices. Similarly, where the elements of the disclosed implementations are implemented using software programming or software elements, the systems and techniques can be implemented with a programming or scripting language, such as C, C++, Java, JavaScript, assembler, or the like, with the various algorithms being implemented with a combination of data structures, objects, processes, routines, or other programming elements.

Functional aspects can be implemented in algorithms that execute on one or more processors. Furthermore, the implementations of the systems and techniques disclosed herein could employ a number of conventional techniques for electronics configuration, signal processing or control, data processing, and the like. The terms "system" as used herein and in the figures, but in any event based on their context, may be understood as corresponding to a functional unit implemented using software, hardware (e.g., an integrated circuit, such as an ASIC), or a combination of software and hardware. In certain contexts, such systems or mechanisms may be understood to be a processor-implemented software system or processor-implemented software mechanism that is part of or callable by an executable program, which may itself be wholly or partly composed of such linked systems or mechanisms.

Implementations or portions of implementations of the above disclosure can take the form of a computer program product accessible from, for example, a computer-usable or computer-readable medium. A computer-usable or computer-readable medium can be a device that can, for example, tangibly contain, store, communicate, or transport a program or data structure for use by or in connection with a processor. The medium can be, for example, an electronic, magnetic, optical, electromagnetic, or semiconductor device.

Other suitable mediums are also available. Such computer-usable or computer-readable media can be referred to as non-transitory memory or media and can include volatile memory or non-volatile memory that can change over time. The quality of memory or media being non-transitory refers to such memory or media storing data for some period of time or otherwise based on device power or a device power cycle. A memory of an apparatus described herein, unless otherwise specified, does not have to be physically contained by the apparatus, but is one that can be accessed remotely by the apparatus, and does not have to be contiguous with other memory that might be physically contained by the apparatus.

While the disclosure has been described in connection with certain implementations, it is to be understood that the disclosure is not to be limited to the disclosed implementations but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A system for monitoring an ophthalmic condition, comprising:
- a headset including a display and an ophthalmic testing unit comprising one or more sensors to obtain sensor information indicating a physiological measurement of an eye of the user; and
- a device including a processor configured by instructions stored in memory to:
  - receive surgical information, from a data structure, corresponding to a first time in which the physiological measurement of the eye is obtained, wherein the surgical information includes a baseline physiological measurement obtained in connection with an ophthalmic procedure;
  - receive sensor information, from the headset, corresponding to a second time in which the physiological measurement is obtained, wherein the headset is configured to present a visual test stimulus via the display while obtaining the sensor information; and
  - generate an ophthalmic score representing post-procedure recovery based on a comparison between the surgical information and the sensor information.

2. The system of claim 1, wherein the processor is further configured by instructions stored in memory to:
- trigger an alert based on the ophthalmic score exceeding a range.

3. The system of claim 1, wherein the processor is further configured by instructions stored in memory to:
- trigger an alert based on the ophthalmic score, the alert includes outputting a message to at least one of the device or the headset.

4. The system of claim 1, wherein the processor is further configured by instructions stored in memory to:
- generate a recommendation based on the ophthalmic score.

5. The system of claim 1, wherein the device is a mobile device in communication with the headset.

6. The system of claim 1, wherein the headset is at least one of a virtual reality (VR), augmented reality (AR), or mixed reality (MR) headset.

7. The system of claim 1, wherein the second time occurs after the first time with the ophthalmic score representing a post-surgical evaluation.

8. The system of claim 1, wherein the processor is further configured by instructions stored in memory to:
- receive updated sensor information from the headset; and
- update the ophthalmic score based on the updated sensor information.

9. The system of claim 1, wherein the processor is further configured by instructions stored in memory to:
- invoke a machine learning model to determine, based on the sensor information, recovery of the eye.

10. The system of claim 1, wherein the processor is further configured by instructions stored in memory to:
- invoke a machine learning model to determine, based on the sensor information, a symptom of the ophthalmic condition.

11. The system of claim 1, wherein the physiological measurement comprises a measure of at least one of visual acuity, drooping eye lids, blink pattern, blood vessels, inflammatory cells, intraocular pressure (IOP), muscle movement, corneal curvature, or pupil response.

12. The system of claim 1, wherein the headset exercises the eye before obtaining the sensor information.

13. The system of claim 1, wherein the ophthalmic testing unit includes a pupil detector, a beam splitter, and an illuminator.

14. The system of claim 1, wherein the ophthalmic testing unit measures blink frequencies, intervals between blinks, and length of blinks.

15. A method for monitoring an ophthalmic condition, comprising:

receiving surgical information, from a data structure, corresponding to a first time in which a physiological measurement of an eye of a user is obtained, wherein the surgical information includes a baseline physiological measurement obtained in connection with an ophthalmic procedure;

receiving sensor information, from a headset worn by a user, corresponding to a second time in which the physiological measurement of the eye is obtained, wherein the headset includes a display and an ophthalmic testing unit comprising one or more sensors to obtain the sensor information indicating the physiological measurement of the eye, wherein the headset presents a visual test stimulus via the display in connection with obtaining the sensor information; and generating an ophthalmic score representing post-procedure recovery based on a comparison between the surgical information and the sensor information.

16. The method of claim 15, further comprising:

triggering a first alert based on the ophthalmic score falling below a lower threshold and a second alert based on the ophthalmic score exceeding an upper threshold.

17. The method of claim 15, further comprising:

receiving, periodically, updated sensor information from the headset; and updating the ophthalmic score based on the updated sensor information.

18. The method of claim 15, further comprising:

invoking a machine learning model to determine, based on the sensor information, a symptom of the ophthalmic condition.

19. The method of claim 15, further comprising:

triggering an alert based on the ophthalmic score, wherein the alert includes displaying a message to a device in communication with the headset.

20. The method of claim 15, further comprising:

configuring the headset to exercise the eye before obtaining sensor information.

21. The system of claim 1, wherein the sensor information includes a physiological response of the eye measured during presentation of the visual test stimulus, and wherein the ophthalmic score is generated based on the comparison between the physiological response and the baseline physiological measurement.

22. The system of claim 1, wherein the ophthalmic score represents a change between the baseline physiological measurement and the physiological measurement obtained at the second time, and is indicative of improvement, deterioration, or stability of the eye following the ophthalmic procedure.

* * * * *